United States Patent [19]

Sparks

[11] 4,053,780
[45] Oct. 11, 1977

[54] METHOD FOR CALIBRATION OF AN AXIAL TOMOGRAPHIC SCANNER

[75] Inventor: Robert A. Sparks, Palo Alto, Calif.

[73] Assignee: Syntex (U.S.A.) Inc., Palo Alto, Calif.

[21] Appl. No.: 623,861

[22] Filed: Oct. 20, 1975

[51] Int. Cl.$^2$ ............................................. G01N 23/00
[52] U.S. Cl. ................................ 250/445 T; 250/252
[58] Field of Search .................... 250/445 T, 491, 252

[56] References Cited

U.S. PATENT DOCUMENTS

| 3,178,575 | 4/1965 | Koerner | 250/445 T |
| 3,778,614 | 12/1973 | Hounsfield | 250/445 T |

Primary Examiner—Alfred E. Smith
Assistant Examiner—B. C. Anderson
Attorney, Agent, or Firm—Joseph I. Hirsch; William B. Walker

[57] ABSTRACT

The method of calibrating an axial tomographic scanner including frame means having an opening therein in which an object to be examined is to be placed, source and detector means mounted on the frame means for directing one or more beams of penetrating radiation through the object from the source to the detector means, and means to rotate the scanner including the source and detector means about the object whereby a plurality of sets of data corresponding to the transmission or absorption by the object of a plurality of beams of penetrating radiation are collected; the calibration method comprising mounting calibration means supporting an adjustable centering member onto the frame means, positioning the adjustable centering member at approximately the center of rotation of the scanner, placing position-sensitive indicator means adjacent the approximately centered member, rotating the scanner and the calibration means mounted thereon at least one time and, if necessary, adjusting the positioning of the centering member until the centering member is coincident with the center of rotation of the scanner as determined by minimum deflection of the position-sensitive indicator means, rotating and translating the source and detector means and determining for each angular orientation of the frame means supporting the source and detector means (a) the central position of each translational scan relative to the centered member and/or (b) if a plurality of detectors are utilized with the detector means for each planar slice of the object being examined, the central position of each translational scan for each detector relative to the centered member.

15 Claims, 3 Drawing Figures

METHOD FOR CALIBRATION OF AN AXIAL TOMOGRAPHIC SCANNER

FIELD OF THE INVENTION

This invention relates to a method for calibrating an axial tomographic scanner. More particularly, this invention relates to a method for calibrating an axial tomographic scanner wherein the need to manually align the center of rotation of the scanner with a linear encoder is obviated. In addition, for each angular orientation of the frame, this invention provides a method for determining the central position of each translational scan relative to a centered member and/or when a plurality of detectors are utilized with the associated detector means for each planar slice of the object being examined, the central position of each translational scan for each detector relative to the centered member.

BACKGROUND OF THE INVENTION

In U.S. Pat. No. 3,778,614 there is described a method and apparatus for examining an object by means of X- or γ-radiation. A commercial embodiment thereof has a source of X-rays adapted to transmit a beam of radiation through a planar slice to be examined, detector means to detect the transmitted beam after it has passed through the object and means to sequentially translate and rotate the source and detector means about the object during radiographic examination. During the set-up and calibration of this apparatus, the center of rotation of the scanner, upon which the source and detector means are mounted, is determined and a linear encoder is manually adjusted so as to align the center of the linear encoder with the center of rotation of the scanner. This procedure only provides for calibration of the central position of one translational scan for one particular rotational orientation of the scanner and, furthermore, does not compensate for irregularities in either the scanner per se or the calibration mechanism at other angular orientations of the scanner. Accordingly, the aforesaid calibration technique does not provide measurements by which the axial tomographic system can correct for scanner or calibration means eccentricities which inherently occur at other angular orientations of the scanner.

OBJECTS OF THE INVENTION

It is, therefore, the primary object of this invention to provide a novel method for calibration of an axial tomographic scanner.

It is a further object of the present invention to provide a novel method for calibrating an axial tomographic scanner which eliminates the need to manually align the center of rotation of the scanner with the central position of a linear encoder.

It is a further object of the present invention to provide a novel method for calibrating an axial tomographic scanner wherein the actual central position of a translational scan of the source and detector means is determined for each of a plurality of angular orientations of the scanner relative to member previously positioned at the center of rotation of the scanner.

It is a further object of the present invention to provide a novel method for calibrating an axial tomographic scanner having a source of penetrating radiation and a plurality of detectors wherein, for each angular orientation of the scanner frame supporting the source and plurality of detectors, the central position for each translational scan of the source and the detectors is determined for each detector relative to a member previously positioned at the center of rotation of the scanner.

These and still further objects, features and advantages of the present invention will become apparent upon consideration of the following detailed disclosure.

BRIEF SUMMARY OF THE INVENTION

The above and still further objects, features and advantages of the present invention are achieved, in accordance therewith, by providing an axial tomographic scanner including frame means having an opening therein in which an object to be examined is to be placed, a source of penetrating radiation and detector means mounted on the frame means for directing one or more beams of penetrating radiation through a planar slice of the object from the source to the detector means, and means to rotate the scanner including the source and detector means mounted thereon about the object whereby a plurality of sets of data corresponding to the transmission or absorption by the object of a plurality of beams of penetrating radiation are collected, and calibrating the aforesaid scanner by mounting calibration means supporting an adjustable centering member onto the frame means, positioning the adjustable centering member at approximately the center of rotation of the scanner, placing position-sensitive indicator means adjacent the approximately centered member, rotating the scanner and calibration means mounted thereon at least one time and, if necessary, adjusting the positioning of the centering member until the centering member is coincident with the center of rotation of the scanner as determined by minimum deflection of the position-sensitive indicator means when maintained in at least substantial contact with the centered member, and rotating the source and detector means and determining for each angular orientation of the frame means supporting the source and detector means (a) the central position of each translational scan relative to the centered member and/or (b) if a plurality of detectors are utilized with the detector means for each planar slice of the object being examined, the central position of each translational scan for each detector relative to the centered member. In actual practice, the positioning of the adjustable centering member at approximately the center of rotation of the scanner and the placement of the position-sensitive indicator means adjacent the approximately centered member are manual operations. After rotation of the scanner further adjustment of the position of the centering member, if necessary, is also a manual operation. However, once it has been determined that the centering member is coincident with the center of rotation of the scanner, as determined by minimum deflection of the position-sensitive indicator means, the subsequent determination of the various central position of each translational scan is conducted automatically by the data processing means associated with the axial tomographic system, and the results thereof are stored in data storage means for subsequent use in determining attenuation coefficients for each of a plurality of individual matrix elements corresponding to the planar slice of the object being analyzed. In particular, for each rotation and translation of the frame means, and the source and detector means mounted thereon, the actual central position of each translational scan (for that particular angular orientation of the scanner) is determined by the maximum decrease in transmission (or conversely the maximum increase in absorption) caused by the beam of penetrating radiation crossing the now-accurately positioned centering member, and this decrease (or increase) is correlated with a particular position on an associated linear encoder. This determination and correlation is repeated for each angular orientation of the scanner relative to the centered member and, if a plurality of detectors are utilized with the detector means, as in a fan-beam system, the central position of each translational scan for each detector is determined at each angular orientation of the scanner. All such data are stored in data storage means and subsequentially utilized during data processing of the transmission or absorption data originally obtained with the scanner (i.e., the raw data) so as to provide an accurate reconstruction of the planar slice of the object undergoing examination.

As indicated above, the central position for each translational scan is determined relative to the accurately positioned centered member for each angular orientation of the frame means. This can be, for example, at 1° angular rotations (particularly, for systems where a single beam of radiation is passed, in parallel lines, through the planar slice of the object being examined during the translational scan of the source and detector means), or it can be at multi-angular rotations (particularly where a fan-beam of penetrating radiation is passed through the object to a plurality of detectors, for example, at 12° angular rotations where 12 detectors, excluding the reference detector, at 1° angular spacings are utilized).

As set forth above, the measured central position of each translational scan (optionally for each of a plurality of detectors) is stored in data storage means and subsequently utilized during data processing of the transmission or absorption data originally obtained with the scanner so as to provide highly accurate reconstructions of the planar slice of the object undergoing examination.

BRIEF DISCRIPTION OF THE DRAWINGS

The features and advantages of the present invention will become more apparent from the following detailed description, taken together with the accompanying drawings wherein.

Figure 1:
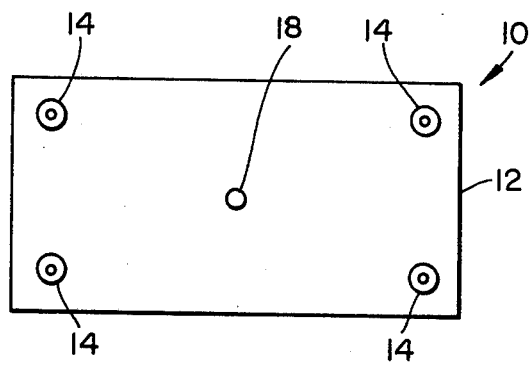
FIG. 1 is a front elevational view of an exemplary calibration means according to the present invention.
Figure 2:
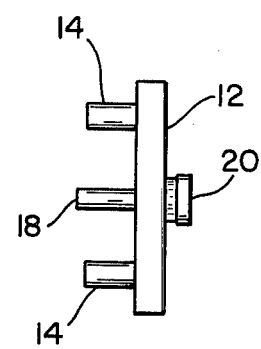
FIG. 2 is a right side elevational view of the calibration means of FIG. 1.

Referring to FIGS. 1 and 2, there is shown calibration means 10 having a backing plate 12 and four cylindrical rods 14, one adjacent to each rectangular corner of backing plate 12, which are adapted for securing backing plate 12 to the frame adjacent the object-receiving opening in an axial tomographic scanner. A centering member 18 is adjustably mounted on backing plate 12 by means of rotatable threads 20 on the reverse side of backing plate 12. Set screws (not shown) on the centering member unit are utilized to adjust the X- and Y-coordinates of the centering member.

Figure 3:
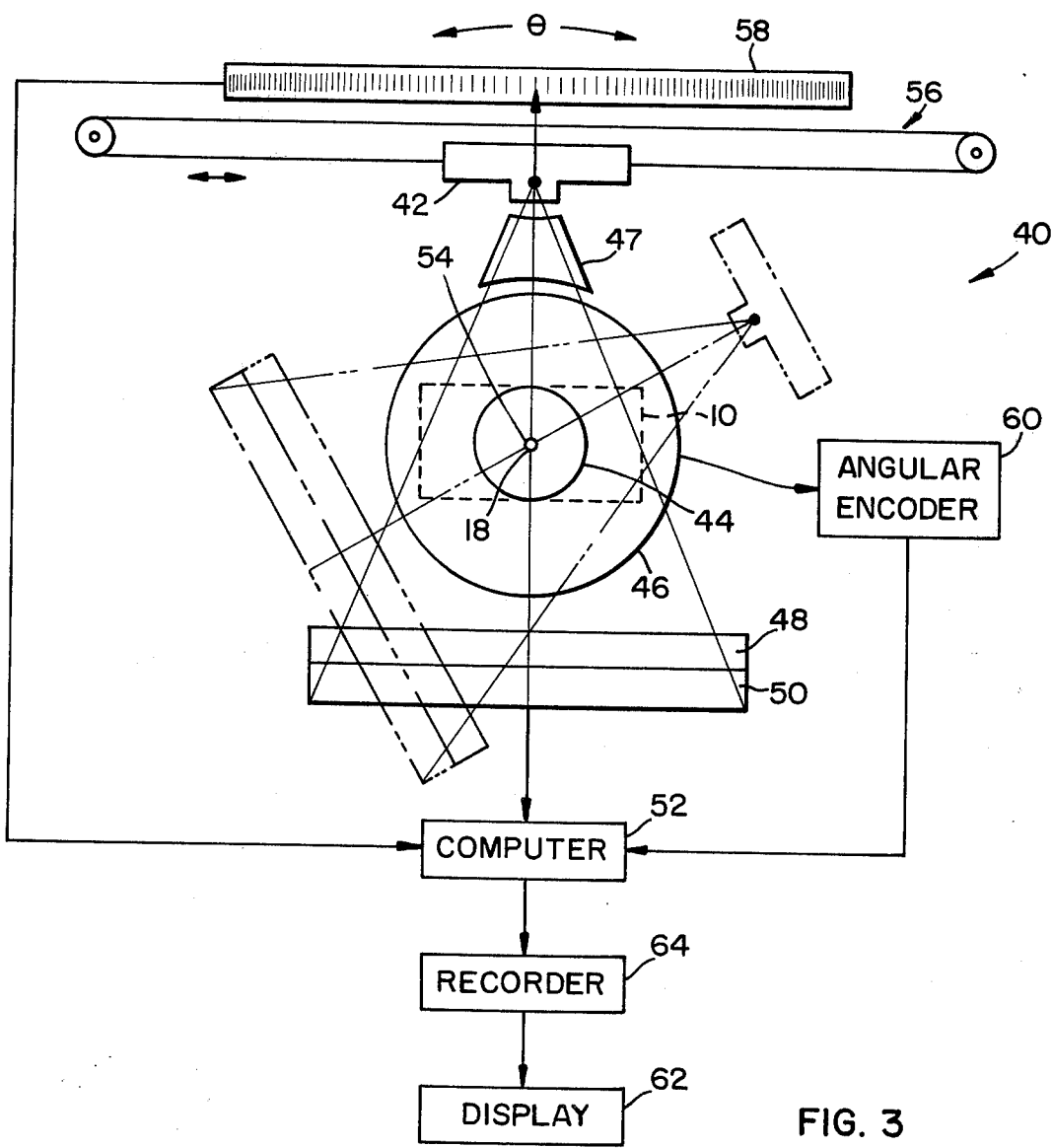
FIG. 3 is a schematic view of an axial tomographic scanner system exemplifying the calibration method of the present invention.

Referring to FIG. 3, there is shown the scanner portion 40 of an axial tomographic system including an X-ray source 42 which directs a fan-shaped beam of X-rays through a planar slice of an object 44 (for example the head or body portion of a patient) which is to be examined. As shown, the object is surrounded by a support 46 which is generally filled with water, the support, in turn, being surrounded by a plastic block (not shown). The plastic block has a cylindrical opening therein which surrounds the outside of the support 46 and rotates around the support which remains stationary along with the object during the radiographic procedure. A radial collimator 47 between source 42 and object 44 collimates the beam of X-rays into a fan-shaped array of a plurality of smaller beams, for example, 12 smaller beams each having a depth (direction into the paper) of about one centimeter and a thickness in the plane of the fan of about 1.2 millimeters. A collimator 48 between object 44 and detector 50 reduces detection of Compton scattered radiation emanating from the object undergoing analysis. Detector 50 can have, for example, an array of photon detectors disposed at the output end of collimator 48 to detect individual beams of radiation passing through object 44 and collimator 48 to the respective detectors. The output from the various detectors is fed, in a known manner, to data storage and processing means 52.

In the embodiment shown in FIG. 3, scanner 40 both rotates and translates about object 44 to be analyzed. More particularly, scanner 40 rotates about an axis of revolution 54 (perpendicular to the plane of the drawing) which preferably passes through the central region of the planar slice of the object being examined. This axis of rotation has been previously determined by placement of calibration means 10 on the frame of scanner 40 in a manner described herein. Angular rotation of scanner 40 is indicated by the angle $\theta$ on the drawing. Additionally, the fan-shaped beam of radiation is scanned laterally across object 44 for each angular orientation of scanner 40. More particularly, for each angular orientation of the scanner, source 42 is moved laterally by means of belt drive 56 and the precise lateral positioning of source 42 is detected by lateral positional encoder 58 which is read optically, the output thereof being fed to one input of data storage and processing means 52. In a similar manner, the angular orientation of the scanner is determined by angular position encoder 60, the optical output of which is also fed to data storage and processing means 52. In an exemplary system, detector means 50 has 12 individual detectors, exclusive of the reference detector, and scanner 40 is rotated in successive 12° increments about object 44. Between successive rotations, source 42 and detector 50 on opposite sides of object 44 are translated across the lateral dimension of the object being analyzed. This process is repeated until sufficient data is obtained which, when processed according to known techniques by data storage and processing means 52, or a series of data storage and processing units 52, yields a sufficient number of attenuation coefficients for each of a plurality of individual matrix elements of the planar slice of the object being analyzed so as to provide a reconstruction of the interior configuration thereof by display means 62 after the processed data has been recorded and stored in recorder means 64.

The calibration method of this invention will now be described with reference to FIG. 3. For a particular given angular orientation of scanner 40, for example as shown in solid outline in FIG. 3, calibration means 10 is secured to the frame of the scanner and central member 18 manually positioned at approximately the center of rotation of the scanner. Thereafter, position-sensitive indicator means, such as a well-known dial indicator, not in contact with the frame (i.e., independent thereof, for example, solidly supported from the floor or on another object which is solidly supported by the floor) is placed adjacent the approximately centered member, and the scanner and calibration means mounted thereon are rotated at least one time and, if necessary, the centering member is manually adjusted and the rotation and adjustment process repeated until the centering member is coincident with the center of rotation of the scanner as determined by minimum deflection of the dial indicator. Thereafter, for a given angular orientation of the scanner, for example, once again as shown in solid outline, source 42 is laterally translated across the transverse dimension of object 44 and the central position of the rotational scan (as determined by the maximum decrease in the transmission or the maximum increase in absorption of the beam of penetrating radiation due to the presence of centered member 18) is correlated with a reading on linear encoder 58, and the resultant measured central position is stored in data storage and processing means 52. The scanner is then rotated to a different angular position, for example as shown in dotted outline in FIG. 3, and this process of linear translation repeated whereby, generally, a slightly different central position for this translational scan will be determined by the linear encoder 58 and stored in data storage and processing means 52. This procedure is repeated for each of the angular positions which will be assumed by the scanner during subsequent examination of an actual object. In this manner, a central position is determined for each translational scan of source 42 whereby transmission or absorption data subsequentially obtained with the system can be accurately correlated with the center of rotation of the scanner and, thereby, accurate reconstructions of the body undergoing examination can be obtained. In addition, as with the system shown in FIG. 3, the central position of each translational scan for each detector in a multi-detector array can be determined relative to the centered member. This provides further correlation data, also stored in data storage and processing means 52, which is useful in the formation of highly accurate reconstructions of the planar slice of the object undergoing analysis.

The calibration method described herein is applicable for use in conjunction with axial tomographic scanners of diverse configurations. For example, in one configuration the scanner has a source of X- or γ-radiation adapted to transmit a beam of radiation through a planar slice of the object to be examined, detector means to detect the transmitted beam after it has passed through the object, and means to sequentially translate and rotate the source and detector means about the object during the radiographic examination. Such a scanner is shown, for example, by U.S. Pat. No. 3,778,614. In a different configuration, as shown by copending application Ser. No. 528,026, filed Nov. 29, 1974, in the name of Douglas Boyd et al, a fan-shaped beam of penetrating radiation is directed through the slice of the object to be analyzed to radiation-sensitive detector means having a plurality of individual detectors for deriving a set of data corresponding to the transmission or absorption of the penetrating radiation by the object along a plurality of divergent lines extending from the source to the detector. A number of sets of such data are obtained for different angles of rotation of the fan-shaped beam relative to the center of the slice being analyzed. Fan-beam irradiation can also be used in conjunction with scanners which require lateral translation of the source and detector. The calibration method of the present invention is applicable for use in conjunction with either of the aforesaid configurations, other computerized axial tomographic configurations which may differ from the above configurations, or other X-ray or γ-ray diagnostic apparatus and configurations which require accurate correlation of a plurality of central positions of translational scans for each of plurality of angular orientations of a source and detector means relative to the center of rotation of the scanner. U.S. Pat. No. 3,778,614 and copending application Ser. No. 528,026, filed Nov. 29, 1974 are incorporated herein by reference to the extent necessary to complete, or render fully understandable, the disclosure hereof.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A method of calibrating an axial tomographic scanner including frame means having an opening therein for receiving an object to be examined, a source of penetrating radiation and detector means mounted on the frame means for directing one or more beams of penetrating radiation from the source to the detector means, means to rotate the frame means including the source and the detector means mounted thereon about the opening and means to translate the source and the detector means laterally across the opening between successive rotations of the frame means by the rotation means; said method comprising positioning a centering member coincident with the center of rotation of the frame means for a first angular orientation thereof; rotating the frame means about the opening and the positioned centering member therein and translating the source and detector means laterally across the opening; and determining for each of a plurality of different angular orientations of frame means the central position of each translational scan relative to centered member.

2. The method of claim 1 wherein the positioning of the centering member coincident with the center of rotation of the frame means comprises mounting calibration means supporting an adjustable centering member onto the frame means, positioning the adjustable centering member at approximately the center of rotation of the frame means, placing position-sensitive indicator means adjacent the approximately centered member, rotating the frame means and the calibration means mounted thereon at least one time and, if necessary, adjusting the positioning of the centering member until the centering member is coincident with the center of rotation of the frame means as determined by observation of minimum deflection of the position-sensitive indicator means when the position-sensitive indicator means is maintained in at least substantial contact with the centered member.

3. The method of claim 1 wherein the source directs a divergent, fan-shaped beam of radiation toward the detector means.

4. The method of claim 1 wherein the central position of each translational scan is determined by detecting the maximum difference in transmission or absorption caused by the penetrating radiation being absorbed by the centered member during lateral translation of the source and detector means.

5. The method of claim 1 further including storing the determined central position of each translational scan in data storage means.

6. A method of calibrating an axial tomographic scanner including frame means having an opening therein for receiving an object to be examined, a source of penetrating radiation mounted on the frame means, detector means mounted on the frame means having a plurality of detectors associated therewith, the source and detector means being adapted for directing a plurality of beams of penetrating radiation from the source to the detector means, means to rotate the frame means including the source and the detector means mounted thereon about the opening, and means to translate the source and the detector means laterally across the opening between successive rotations of the frame means; said method comprising positioning a centering member coincident with the center of rotation of the frame means for a first angular orientation thereof; rotating the frame means about the opening and the positioned centering member therein and translating the source and detector means laterally across the opening; and determining for each of the plurality of detectors at each of a plurality of different angular orientations of said frame means the central position of each translational scan relative to said centered member.

7. The method of claim 6 wherein the positioning of the centering member coincident with the center of rotation of the frame means comprises mounting calibration means supporting an adjustable centering member onto the frame means, positioning the adjustable centering member at approximately the center of rotation of the frame means, placing position-sensitive indicator means adjacent the approximately centered member, rotating the frame means and the calibration means mounted thereon at least one time and, if necessary, adjusting the positioning of the centering member until the centering member is coincident with the center of rotation of the frame means as determined by observation of minimum deflection of the position-sensitive indicator means when the position-sensitive indicator means is maintained in at least substantial contact with the centered member.

8. The method of claim 6 wherein the source directs a divergent fan-shaped beam of radiation toward the detector means.

9. The method of claim 6 wherein the central position of each translational scan is determined by detecting the maximum difference in transmission or absorption caused by the penetrating radiation being absorbed by the centered member during lateral translation of the source and detector means.

10. The method of claim 6 further including storing in data storage means the determined central position for each of the detectors for each translational scan at each angular orientation of the frame means.

11. The method of calibrating an axial tomographic scanner including means having an opening therein for receiving an object to be examined, a source of divergent penetrating radiation mounted on the frame means, detector means having a plurality of detectors associated therewith for receiving the penetrating radiation directed thereto from the source, means to rotate the frame means including the source mounted thereon about the opening; said method comprising positioning a centering member coincident with the center of rotation of the frame means for a first angular orientation thereof; rotating the frame means about the opening and the positioned centering member therein; and determining the position of the centering member at each of a plurality of different angular orientations of the frame means relative to the opening.

12. The method of claim 11 wherein the positioning of the centering member coincident with the center of rotation of the frame means comprises mounting calibration means supporting an adjustable centering member onto the frame means, positioning the adjustable centering member at approximately the center of rotation of the frame means, placing position-sensitive indicator means adjacent the approximately centered member, rotating the frame means and the calibration means mounted thereon at least one time and, if necessary, adjusting the positioning of the centering member until the centering member is coincident with the center of rotation of the frame means as determined by minimum deflection of the position-sensitive indicator means when the position-sensitive indicator means is maintained in at least substantial contact with the centered member.

13. The method of claim 11 wherein the source directs a fan-shaped beam of radiation toward the detector means.

14. The method of claim 11 wherein the position of the centering member is determined for each of the plurality of angular orientations of the frame means by detecting the maximum difference in transmission or absorption caused by the penetrating radiation being absorbed by the centered member at each of the angular orientations.

15. The method of claim 11 further including storing in data storage means the determined position of the centering member for each of the plurality of angular orientations of the frame means relative to the opening.

* * * * *